United States Patent
Hellmuth et al.

(10) Patent No.: US 7,084,986 B2
(45) Date of Patent: Aug. 1, 2006

(54) SYSTEM FOR MEASURING THE OPTICAL IMAGE QUALITY OF AN EYE IN A CONTACTLESS MANNER

(75) Inventors: Thomas Hellmuth, Aalen (DE); Lieng-Chuong Tan, Aalen (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 10/129,255

(22) PCT Filed: Aug. 31, 2001

(86) PCT No.: PCT/EP01/10070

§ 371 (c)(1),
(2), (4) Date: Oct. 1, 2003

(87) PCT Pub. No.: WO02/17775

PCT Pub. Date: Mar. 7, 2002

(65) Prior Publication Data
US 2004/0061830 A1 Apr. 1, 2004

(30) Foreign Application Priority Data
Aug. 31, 2000 (DE) ............................ 100 42 751

(51) Int. Cl.
*G01B 9/02* (2006.01)
*A61B 3/10* (2006.01)

(52) U.S. Cl. .................. 356/479; 356/497; 351/221
(58) Field of Classification Search ............ 356/477, 356/479, 482, 496, 497; 351/221
See application file for complete search history.

(56) References Cited

U.S. PATENT DOCUMENTS

| 4,938,584 A | * | 7/1990 | Suematsu et al. ............ 351/211 |
| 5,321,501 A | * | 6/1994 | Swanson et al. ............ 356/479 |
| 5,329,321 A | | 7/1994 | Koizumi |
| 5,633,694 A | * | 5/1997 | Mihashi et al. ............. 351/211 |

(Continued)

FOREIGN PATENT DOCUMENTS

WO WO 95/33970 12/1995

(Continued)

OTHER PUBLICATIONS

"Optical Coherence Tomography" by A. Fercher, *Journal of Biomedical Optics*, vol. 1, No. 2, Apr. 1996, 157-173.

(Continued)

*Primary Examiner*—Gregory J. Toatley, Jr.
*Assistant Examiner*—Patrick J. Connolly
(74) *Attorney, Agent, or Firm*—Reed Smith LLP

(57) ABSTRACT

A system is used for contactless measurement of the optical imaging quality of an eye with an interferometer by which at least one light pulse with a short coherence length is coupled into the eye from a light source. The optical path length of at least one arm of the interferometer is varied for measuring the length of the eye until a typical interference pattern between a reflection of the cornea and a reflection of the retina of the eye occurs in a detector. This interference pattern together with a known path segment of the variation of the optical path length allows conclusions to be made about the length of the eye. The variation of the optical path length is carried out by introducing at least partially optically transparent elements and by at least one element of the interferometer which is movable in a defined manner in at least one of the light paths of the interferometer.

21 Claims, 4 Drawing Sheets

U.S. PATENT DOCUMENTS

| | | | | |
|---|---|---|---|---|
| 5,644,642 | A | * | 7/1997 | Kirschbaum .................. 382/103 |
| 5,847,827 | A | * | 12/1998 | Fercher ........................ 356/493 |
| 5,975,699 | A | * | 11/1999 | Hellmuth ...................... 351/211 |
| 6,002,484 | A | * | 12/1999 | Rozema et al. .............. 356/515 |
| 6,053,613 | A | * | 4/2000 | Wei et al. .................... 351/205 |
| 6,098,887 | A | * | 8/2000 | Figarella et al. ......... 235/472.01 |
| 6,137,585 | A | * | 10/2000 | Hitzenberger et al. ...... 356/484 |
| 6,144,456 | A | * | 11/2000 | Chavanne et al. ........... 356/479 |
| 6,191,862 | B1 | * | 2/2001 | Swanson et al. ............. 356/450 |
| 6,608,717 | B1 | * | 8/2003 | Medford et al. ............. 359/368 |
| 6,779,891 | B1 | * | 8/2004 | Barth et al. ................. 351/212 |

FOREIGN PATENT DOCUMENTS

| WO | WO 96/35100 | 11/1996 |
|---|---|---|
| WO | WO 00/28884 | 5/2000 |
| WO | WO 00/43730 | 7/2000 |

OTHER PUBLICATIONS

"Measurement Equipment for Determining the Monochromatic Aberration of the Human Eye" by P. Mierdel, H. E. Krinke, W. Wiegand, M. Kaemmerer, T. Seller, *Der Ophthalmologie*, vol. 94, Jun. 1997, 441-445.

"Objective measurement of wave aberrations of the human eye with the use of a Hartmann-Shack wave front sensor" by J. Liang, B. Grimm, S. Goelz, J. F. Bille, *J. Opt. Soc. Am. A*, vol. 11, No. 7, Jul. 1994.

* cited by examiner corneal reflex

SYSTEM FOR MEASURING THE OPTICAL IMAGE QUALITY OF AN EYE IN A CONTACTLESS MANNER

CROSS-REFERENCE TO RELATED APPLICATIONS

This application claims priority of International Application No. PCT/EP01/10070, filed Aug. 31, 2001 and German Application No. 100 42 751.0, filed Aug. 31, 2000, the complete disclosures of which are hereby incorporated by reference.

BACKGROUND OF THE INVENTION a) Field of the Invention

The invention is directed to a system for contactless measurement of the optical imaging quality of an eye with an interferometer by which at least one light pulse with a short coherence length is coupled into the eye from a light source.

b) Background of Problems Relating to the Invention

Following operations in the region of the lens of the eye and the cornea, for example, cataract operations or refractive procedures on the cornea, optical deviations or aberrations can occur in the visual system of the eye which can not be corrected by spherical or astigmatic lenses or cylindrical lenses. Another problem with these aberrations is that they increase dramatically as the pupil diameter increases and thus seriously impair night vision in particular.

Therefore, it is important to detect these aberrations by measurement techniques in order to be able to initiate appropriate corrective measures already during the operation if possible. Further, in the case of cataract operations in which the original lens has been removed and replaced by an artificial lens, it is very important to measure the length of the eye in order to select an appropriate synthetic replacement lens which is adapted to the length of the eye and thus enables good vision.

Since these measurements of the imaging quality of the eye have an effect on the lens in its interaction with the eye length as well as on the aberrations and are to be carried out during and/or shortly after the operation, only noncontacting or contactless methods may be applied for the sake of quality assurance in order to prevent tissue irritation and infection. Therefore, the measurement of the length of the eye by ultrasound as was commonly performed heretofore is ruled out because it requires an ultrasound head to be placed on the cornea.

c) Description of the Related Art

The article "Optical Coherence Tomography" by A. Fercher, *Journal of Biomedical Optics*, Vol. 1, No. 2, April 1996, 157–173, describes a method for analyzing the length of the eye in contactless mode.

By means of a two-arm interferometer, e.g., a Michelson interferometer, light is coupled into the eye to be measured as continuous light or at least in the form of short light pulses or wavetrains. Interference can be brought about between a light reflection originating from the cornea and a light reflection originating from the retina in the area of a sensing device by means of a given difference in arm length of the interferometer which approximately corresponds to the anticipated length of the human eye, usually between 24 mm and 28 mm. A reflector in the area of the interferometer can be measured by a measuring device, or scanner, until the desired interference pattern between the retinal and corneal reflections comes about. The measurable movement path required for this purpose together with the known starting position and the known preserved difference in arm length of the interferometer gives a quantity which makes it possible for accurate conclusions to be made about the length of the measured eye, that is, the distance between the surface of the cornea and the surface of the retina.

However, it is disadvantageous that only the length of the eye can be measured by this approach.

U.S. Pat. No. 5,975,699 describes a method and a device which simultaneously measures the length of the eye and the refractive error. This device, which is capable of measuring the length of the eye and the refractive error simultaneously, couples light into the interior of the eye via a Michelson interferometer with a predetermined length difference between the two intersecting optical arms and via an additional beam splitter. The corneal and retinal reflections then arrive partly unused in the interferometer via this beam splitter; the other part which is used for measurement arrives, via an optical imaging device, at a grating where a spectral division of the light takes place. Subsequently, a spectral evaluation of this light is carried out in order to determine the refractive error of the eye and to evaluate the intensity variations of the corneal and retinal reflections generated by the interference due to the different path lengths of the interferometer in order to determine the length of the eye.

Both of the methods mentioned above have in common that they are incapable of detecting greater deviations of the visual system through measurement techniques. In addition, an external interferometer with an arm length difference corresponding to the optical length of the eye to be investigated is applied in both methods. A basic feature of the interferometer consists in that fifty percent of the light is lost at the beam splitter and good perceptibility of the signals is impaired by the resulting attenuation of the intensity of the light and of the reflections introduced. Moreover, a Michelson interferometer is complicated to set up and handle.

A method for analyzing optical deviations in an eye is described in the article "Measurement Equipment for Determining the Monochromatic Aberration of the Human Eye" by P. Mierdel, H. E. Krinke, W. Wiegand, M. Kaemmerer, T. Seiler, *Der Ophthalmologie*, Vol. 94, June 1997, 441–445.

In this case, a uniform pattern of light points is generated on the fundus oculi in the area of the retina of the eye to be examined by focusing light beams generated by a perforated mask through a collector lens at a short distance from the retina. In an ideal eye, this causes a uniform pattern of light points on the retina. In an eye with corresponding aberrations in the region of the lens or cornea, however, a distorted pattern of light points is brought about on the retina. An intermediate image of the retinal light point pattern is then generated via corresponding optical imaging devices and is imaged on a light-sensitive CCD sensor by a camera objective. The imaging of the light point pattern is distorted when the visual system has optical aberrations. These aberrations can be numerically analyzed. The results are displayed as a list of weighting factors of Zernike polynomials by which a wavefront aberration topography can be modeled.

Another method is described in the article "Objective measurement of wave aberrations of the human eye with the use of a Hartmann-Shack wave front sensor" by J. Liang, B. Grimm, S. Goelz, J. F. Bille, *J. Opt. Soc. Am. A*, Vol. 11, No. 7, July 1994.

By means of a reflection of introduced light, a secondary light source in the area of the retina is generated on the fundus of the eye to be examined. The light beam bundle of the retinal reflection is then concentrated on a CCD target by a lens arrangement, or lens array, as it is called. The light beam bundle exiting from the pupil is composed of parallel rays in an emmetropic eye, that is, an ideal or healthy eye without aberrations. Therefore, in an emmetropic eye the rays which are bundled through the lens array show a uniform grid-like pattern of light points. When there are aberrations in the visual system, individual rays from the bundle of rays have deviations from their ideal direction or parallelism because of the deviation of the wavefront of the light exiting from the pupils of the eyes. Thus, in an eye with aberrations, the light point pattern deviates from the uniform pattern of the emmetropic eye. These deviations can then be numerically analyzed in order to obtain weighting factors of Zernike polynomials.

The last two methods mentioned above make it possible to measure aberrations of the visual system. However, they are disadvantageously limited to measurement of these aberrations only and can not measure the length of the human eye.

OBJECT AND SUMMARY OF THE INVENTION

Therefore, it is the primary object of the invention to provide a system for contactless measurement of the optical imaging quality of an eye during and after operations in the region of the lens and/or cornea which supply as much information as possible so as to enable, by way of the operation or subsequent corrective measures, the most ideal possible vision under at least approximately all occurring light conditions.

According to the invention, this object is met in that the imaging quality of an eye is measured by at least one light pulse with a short coherence length which is coupled into the eye by an interferometer. The optical path length of at least one arm of the interferometer is varied for measuring the length of the eye until a typical interference pattern between a reflection of the cornea and a reflection of the retina of the eye occurs in a detector. Together with a known path segment of the variation of the optical path length, this allows conclusions to be made about the length of the eye. The variation of the optical path length is carried out by introducing at least partially transparent elements and by at least one element of the interferometer which is movable in a defined manner in at least one light path of the interferometer.

In the system according to the invention, the measurement of the length of the eye can take place directly in the interferometer. For this purpose, according to the invention, the optical path length of at least one arm of the interferometer is varied by at least partially optically transparent elements and by at least one element which is movable in a defined manner and which, depending on the construction of the invention, can be either a reflector or a sensor; whether a reflector or a sensor is used in unimportant as concerns the functioning of the interferometric measurement. By introducing the elements which are at least partially optically transparent and which, for example, can be constructed as cylinders of polymethylmethacrylate (PMMA) in a particularly advantageous embodiment form of the invention, the optical length is changed corresponding to the transit or running length of the light and corresponding to the index of refraction in the at least partially transparent material of the elements. Therefore, in order to determine interference, the reflector need only be moved by a very small path segment, depending on the optical element that is introduced, until the interference pattern occurs.

Accordingly, in a particularly advantageous manner, a very fast measurement can be carried out because the entire length of the eye to be measured, which generally varies between 24 mm and 28 mm, can be divided into several, e.g., four, groups. As a result of the at least partially transparent element which is formed with a different length for each of the groups, the reflector need only be moved by 1 mm for each of the length groups to be measured. If the sensor finds a matching interference pattern during this movement, the same measurement is carried out again in the next group with the next shortest or next longest at least partially transparent element. Accordingly, it is advantageous that the measurement itself which takes place in principle only during the adjustment of the reflector can be carried out within a shorter time period, so that measurement errors which could occur, for example, due to a relative movement between the eye, as object to be measured, and the interferometer are decisively minimized by the reduction in time.

In a particularly advantageous construction and further development of the invention, the reflections of the retina are sent via an optical imaging device to a device for detecting the aberrations of the wavefronts in mydriasis, that is, in the nonparaxial or far-axis areas of the eye.

In a particularly advantageous further development of this construction of the invention, this device can be constructed as a Hartmann-Shack sensor.

There are decisive advantages to this combination of interferometric measurement of the length of the eye and analysis of aberrations which can occur through the cornea and possibly also sometimes through the lens predominantly in the paraxial regions with respect to the axis of the eye. A first decisive advantage is offered through the construction itself, which is capable of carrying out both measurements by means of an individual reference point which is generated by a light source and by a corresponding reflection of the light coupled into the eye. Comparability of the measured values and the possibility of a correlation between the measured values with respect to the aberrations and with respect to the length of the eye which are based on the same reference point are provided, so that the quality and therefore the practical use of the measurement results for the operator and the patient can be improved.

Further, the combination provides an instrument for measuring all quantities of decisive importance for the imaging quality of the eye and, because of its contactless construction, the device also makes it possible during an operation, e.g., insertion of an intraocular lens implant, to carry out corresponding monitoring, quality assurance and, if necessary, correction of the changes performed by the operator.

The system according to the invention is advantageously applied very quickly and easily and supplies values for eye length which are helpful in selecting the lens for the implant and can simultaneously provide information about aberrations which may possible occur in the region of the cornea so that tensions or stresses which may be generated in the cornea during the operation and which can produce these aberrations as a result of deformations or the like can be quickly counteracted by selection of a suitable lens in that the operator adapts the implant in a corresponding manner or carries out another appropriate corrective measure immediately.

In this specific application where the imaging quality of the eye is measured during the operation, there is the decisive advantage that a detected error can be responded to immediately, so that there is no need for a further operation as would be required for purposes of correction, for instance, if measurement were to take place not until the wounds occurring during the operation had healed.

The risk of an additional operation is reduced, which represents a decisive simplification particularly for older patients who make up the principal target group for cataract operations, since this group of patients is certainly to be considered as an increased-risk group in any form of operation.

DESCRIPTION OF THE PREFERRED EMBODIMENTS

Figure 1:
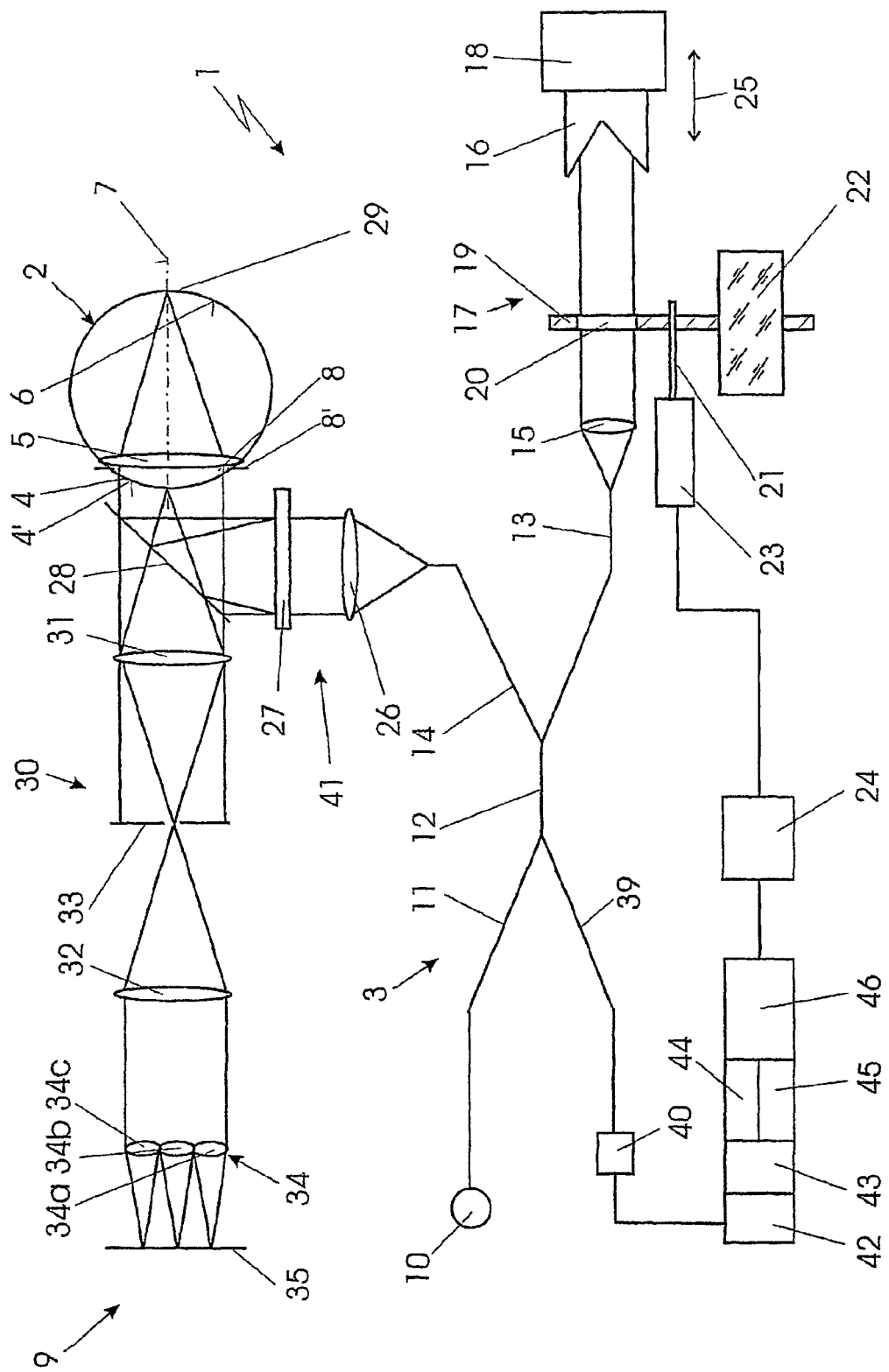
FIG. 1 shows an embodiment form of a system for measuring the optical imaging quality of an eye.

FIG. 1 shows a possible embodiment form of the system 1 for contactless measurement of the optical imaging quality of an eye 2 with an interferometer 3. The system 1 is to be used primarily for measuring the human eye 2 during and after surgical procedures in the region of the cornea 4 and lens 5. However, it is also conceivable in principle to use the system 1 for measuring similarly constructed eyes 2 of other mammals, since the system 1 works automatically in any case and does not require any feedback from the patient or subject. This also makes the system 1 suitable for use during operations in which the patient is generally at least partly anesthetized, in which case feedback would possibly be difficult.

The system 1 is provided for simultaneous measurement of aberrations and of a length L of the eye 2 in a contactless manner, that is, without a probe or the like contacting the eye 2.

By length L of the eye 2 is meant the distance between the surface 4' of the cornea 4, the so-called anterior epithelium, and the fundus with the retina 6.

The aberrations are deviations of the light rays in the eye 2 from the ideal paths of these light rays. These aberrations occur predominantly when light passes through the cornea 2 and are caused by deformations in the cornea 4. Particularly critical in this regard are the nonparaxial regions of the cornea, that is, the regions of the cornea 4 located at a distance from the optic axis 7 of the eye which come into play only when the iris 8' is wide open, that is, with dilated pupil 8 in mydriasis, e.g., under low light conditions.

As can be seen from FIG. 1, the system 1 comprises the interferometer 3 which is constructed as a fiber-optic interferometer 3, a device 9 for detecting aberrations in the wavefronts which is constructed as a Hartmann-Shack sensor 9, and a light source 10 which emits light with a short coherence length.

In the preferred embodiment example according to FIG. 1, the light source 10 is constructed as a superluminescent diode (SLD) which couples its radiation directly into an optical fiber 11 known as connection fiber. The fiber 11 is connected at one of its ends to the end of a 3-dB coupler 12 which splits the radiation into two fibers 13 and 14. The radiation from the end of fiber 13 is collected in a lens 15 and strikes a reflector 16. The light is reflected back from the reflector 16 into the end of fiber 13 and accordingly also into the 3-dB coupler 12.

In the following description, the reflector 16 and the lens 15, which is constructed as a collector lens, are referred to as the reference arm 17 of the fiber-optic interferometer 3. The reflector 16 is arranged on a driven holding element 18 which is preferably movable linearly forward and backward. Further, the reference arm 17 of the fiber-optic interferometer 3 has a revolving wheel 19 between the reflector 16 and the lens 15 which is indicated schematically in cross section in FIG. 1.

Figure 2:
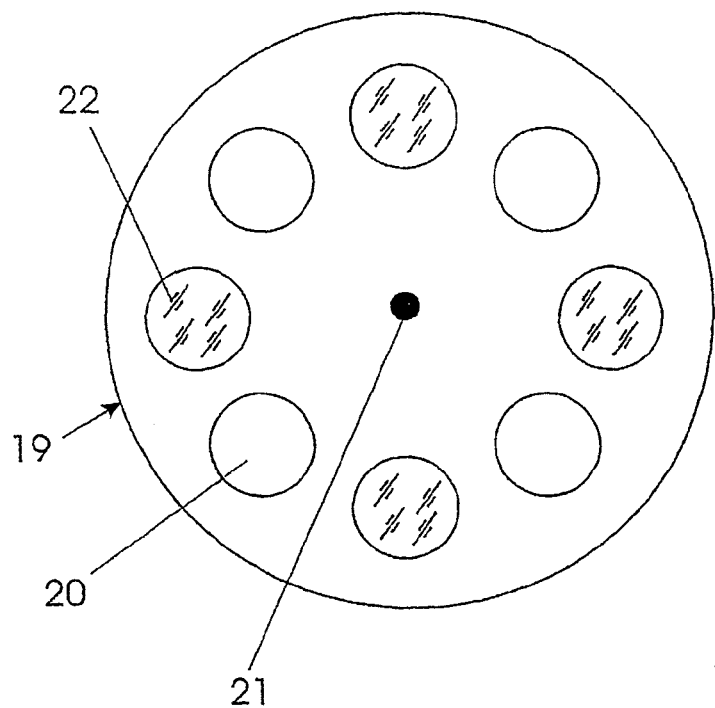
FIG. 2 shows a detailed view of a wheel from FIG. 1.

As is shown in FIG. 2, a plurality of diaphragm openings 20 are introduced in the wheel 19, their centers lying on a circle in whose center a central shaft 21 of the wheel 19 is arranged. Every second diaphragm opening 20 contains an at least partially optically transparent element 22 which is constructed in this case as a transparent cylinder 22 preferably made of PMMA (polymethylacrylate). The transparent cylinders 22 have different lengths l, at least one of the cylinders 22 being constructed with a length $l=L/(n-1)$, where n is the index of refraction of the cylinder 22 of PMMA (e.g., n=1.336). $L=n·l$ is the optical length L of a normal eye 2.

When this transparent cylinder 22 of length l is introduced in the optical path or light beam of the reference arm 17, its optical arm length changes. Ideally, the lengths l of the individual cylinders 22 are consequently so selected that the arm length can be reduced in individual stages over all existing cylinders 22 in such a way that all commonly occurring lengths L of an eye 2 can be covered by the reductions. The reference arm 17 of the interferometer 3 can accordingly be shortened relative to the other arms of the interferometer 2 by the anticipated length L of the eye 2.

The wheel 19 is driven by a stepper motor 23. The frequency of the driving circuit of a controller/regulator 24 of the stepper motor 23 is selected in such a way that the rotation is synchronized with a periodic linear movement 25 of the reflector 16. Therefore, the optical arm length of the reference arm 17 of the fiber-optic interferometer 2 changes periodically between $L_0$ and $L_0+L$, with the reference arm length $L_0$ without the cylinder 22 being introduced.

The light from the end of the fiber 14 is collected by another lens 26 and conducted, via a diffractive optical element (DOE) 27 and a beam splitter 28, to the eye 2 of the patient. The diffractive optical element 27 is so designed that the first diffraction order is focused on the surface 4' of the cornea 4. To ensure that no false measurements occur at least during the actual measurement period, it must be ensured that the surface 4' of the cornea 4 of the eye 2 which is measured remains at a defined constant distance from the system 1 or at least from the diffractive optical element 27. This can be carried out, for example, by means of an appropriate support for the chin and forehead of the patient which is coupled directly to the system 1 as is known, per se, in devices for measuring visual acuity and the like.

The diffraction efficiency of the diffractive optical element 27 is selected in such a way that only about five percent of the impinging light is diffracted in the first diffraction order. The visual system of the eye 2 comprising the cornea 4 and lens 5 concentrates the zeroth diffraction order of the diffractive optical element 27 in the eyeground of the eye 2 on the retina 6 and generates a secondary light source 29 on the retina 6 by reflection.

The light proceeding from this secondary light source 29 on the retina 6, which has only about $10^{-4}$-times the intensity of the light radiated in, is collected in an emmetropic eye 2 through the visual system of the eye 2 in essentially parallel rays which arrive at the beam splitter 28. A portion of the collected radiation is deflected by the beam splitter 28 and guided to the diffractive optical element 27. Due to the low diffraction efficiency of the diffractive optical element 27, the light from the secondary light source 29 on the retina 6 penetrates the diffractive optical element 27 almost without being influenced and is collected through the lens 26 in the end of the fiber 14.

The ray focused on the surface 4' of the cornea 4 is partly reflected by the latter. The reflection factor of the cornea 4 is about four percent. Another five percent of the light reflected by the cornea 4 is collected through the diffractive optical element 27 in a focus. It is therefore deliberately lost for the system, 1, since only the portion of the light arriving at the lens 26 in a parallel manner is concentrated in the end of the fiber 14. Accordingly, the intensity of this flow of light which is reflected by the cornea 4 and collected through the lens 26 in the end of the fiber 14 is also only $10^{-4}$-times the intensity of the input light. Therefore, the light reflected by the cornea 4 is a light having the same intensity as the light of the secondary light source 29 on the retina 6. The two light beams of comparable intensity are then focused in the end of the fiber 14 by means of the collector lens 26.

The other portion of the light which strikes the beam splitter 28 penetrates the latter and passes via an optical imaging device 30 to the device 9 for detecting aberrations in the wavefronts which is constructed in this case as a Hartmann-Shack sensor 9. Accordingly, as a result of the beam splitter 28, the secondary light source 29 on the retina 6 can be used for measuring the length L of the eye 2 and for measuring the aberrations simultaneously.

In the preferred embodiment form shown in FIG. 1, the Hartmann-Shack sensor 9 has the imaging device 30 with two collector lenses 31 and 32, a diaphragm 33, a lens array 34 and a detector field 35 which is preferably formed of CCD sensors.

The collector lens 31 focuses the light rays originating from the secondary light source 29 in the region of the diaphragm 33. The light reflected from the surface 4' of the cornea 4 is divergent and is parallelized through the collector lens 31. These parallel rays of the light reflected from the cornea 4 are cut off through the diaphragm 33. The diaphragm 33 accordingly functions as a beam blocker which eliminates almost all of the light reflected from the cornea 4.

The light of the secondary light source 29 on the retina 6 is focused in the area of the diaphragm 33 and can accordingly penetrate the diaphragm 33 without obstruction. It is then collected by the collector lens 32 to form a parallel beam which strikes the lens array 34. The optical imaging device 30 with the two collector lenses 31 and 32 and the diaphragm 33 accordingly images the pupil 8 of the eye 2 on the plane of the lens array 34. Every individual lens 34a, 34, 34c of the lens array 34, three of which are indicated by way of example, focuses the light beam bundle impinging on each of the lenses 34a, 34, 34c on the detector field 35 with the at least one CCD sensor. A reasonable size for the lens array 34 is about 5×5 to 20×20 individual lenses 34a, 34b, 34c, . . . .

In an emmetropic eye 2 without aberrations, the focal points generated by the individual lenses 34a, 34b, 34c, . . . are equidistant and form a uniform light point pattern. In an eye 2 with aberrations, the light point pattern is correspondingly distorted.

In the following, it will be described in detail how the corresponding measurements are carried out at the eye 2 with the system 1 shown in FIG. 1 and FIG. 2. First, the measurement of aberrations of the eye 2 will be described.

Figure 3:
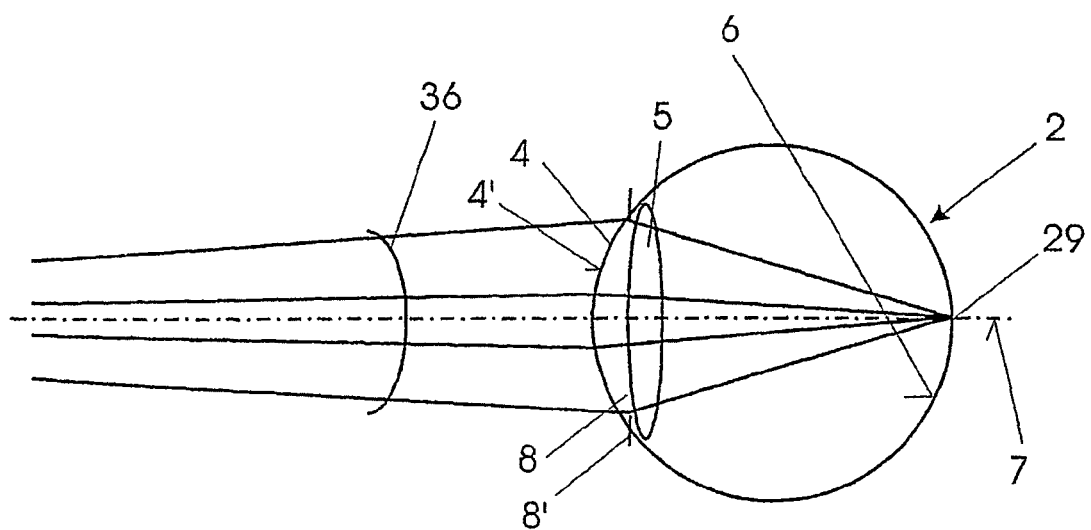
FIG. 3 shows a schematic view of a wavefront error in an eye.

It will be seen in FIG. 3 that the rays of the bundle of rays exiting from the pupil 8 of the eye 2 can be considered as the normals of a surface 36. The surface 36 is considered, as a whole, as a sphere when the rays have a common point of intersection. With aberrations, however, the surfaces 36 considered as a whole are an aspherical body. In principle, this is conceived in such a way that the light beam coupled into the eye 2 via the interferometer 3 has such a small diameter that it penetrates into the eye 2 through the center of the pupil 8. In this way, it can be ensured that the beam undergoes no distortions or alterations when penetrating into the eye 2, since, in general, no aberrations occur in the near-axis or paraxial regions of the cornea 4 and lens 5. This is also particularly advantageous, since aberrations which may possibly occur have no influence on the measurement of the length L of the eye 2 by the interferometer 3 which is described in more detail in the following.

The light beams which exit from the eye again via the visual system also pass through the near-axis area of the pupil 8 in mydriasis, so that possible aberrations which could disadvantageously influence the night vision of the patient in particular can be detected by the Hartmann-Shack sensor 9.

This is indicated schematically in FIG. 3 in that a deviation from the ideal surface in the form of a spherical segment that is more pronounced than in the paraxial and near-axis areas is indicated at the surface 36. The function describing the surface 36 can be described by Zernike polynomials; these are functions in the polar coordinates $\rho$ and $\phi$ in the pupil plane 37 according to FIG. 4. The coordinate $\rho$ is scaled and is assumed to be 0 in the center of the pupil 8 and 1 at the edge of the pupil 8. For the sake of simplicity, only aberrations of the lowest order, or Seidel aberrations, are considered; therefore, eight Zernike polynomials are needed to describe the aspherical surface:

$$f(\rho, \varphi) = \sum_{i=1}^{8} a_i Z_i(\rho, \varphi),$$

where
$Z_1 = \rho \cos \phi$
$Z_2 = \rho \sin \phi$
$Z_3 = 2\rho^2 - 1$
$Z_4 = \rho^2 \cos 2\phi$
$Z_5 = \rho^2 \sin 2\phi$
$Z_6 = (3\rho^2 - 2)\rho \cos \phi$
$Z_7 = (3\rho^2 - 2)\rho \sin \phi$
$Z_8 = 6\rho^4 - 6\rho^2 + 1$, where $Z_1$ and $Z_2$ represent the inclination, $Z_3$ represents the defocusing, $Z_4$ and $Z_5$ represent the astigmatism, $Z_6$ and $Z_7$ represent the asymmetric aberrations or coma, and $Z_8$ represents the spherical aberration.

Figure 4:
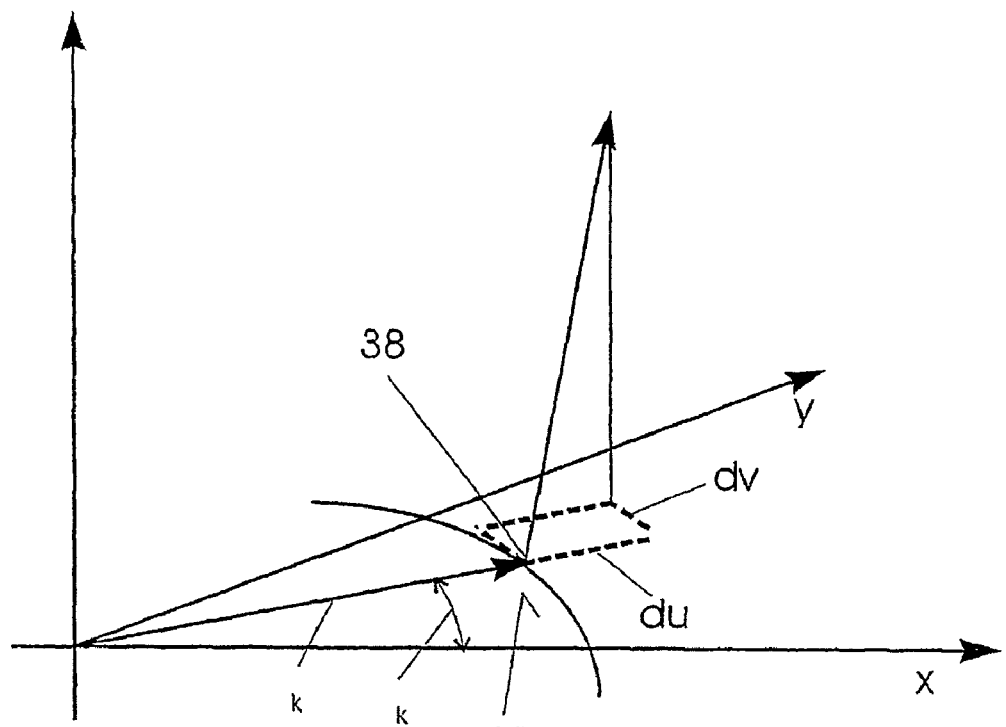
FIG. 4 shows azimuth and radial differentials of rays exiting from a pupil.

The unknown coefficients $a_i$ can be determined when the full differentials of the radial displacement du and the azimuth displacement dv according to FIG. 4 are known at at least four points 38, one of which is shown by way of example, with coordinates $(\rho_k, \phi_k)$, k=1, 2, 3, 4. The differentials du, dv are directly related to the inclination of the surface $f(\rho, \phi)$:

$$grad_\rho f(\rho, \varphi) = \frac{\partial f(\rho, \varphi)}{\partial \rho} = du(\rho, \varphi) \qquad (2)$$

$$grad_\varphi f(\rho, \varphi) = \frac{1}{\rho}\frac{\partial f(\rho_k, \varphi_k)}{\partial \rho} = dv(\rho, \varphi). \qquad (3)$$

These two equations (2), (3) apply to the four rays which intersect the pupil 8 at coordinates ($\rho_k$, $\phi_k$), k=1, 2, 3, 4. Therefore, there are a total of eight equations by which the eight unknown coefficients $a_1$ can be determined.

When aberrations of a higher order are to be determined, additional Zernike polynomials of a higher order must be incorporated. Then, naturally, more than four rays with their differentials are needed to determine all coefficients $a_1$.

In principle, any other wavefront analysis principle, e.g., an interferometer test device, can also be used for the system 1. However, disadvantages must then be taken into account, since interferometer test devices lack a dynamic bandwidth and robustness, as is generally known.

The following remarks describe how the length L of the eye 2 can be measured by means of the system 1 described in FIG. 1 and FIG. 2.

In the system 1, the radiation of the secondary light source 29 on the retina 6 of the eye 2 and the radiation reflected by the reflector 16 are superimposed by the 3-dB coupler 12. The radiation passes through a fiber 39 to a detector 40, which is likewise constructed as a CCD sensor in a particularly advantageous manner, and is recorded by the latter. At the same time, the moving reflector 16 leads to a temporary change in the length of the reference arm 17.

As was already mentioned, the light source 10 is a superluminescent diode (SLD) with a coherence length on the order of 20 μm. A modulated signal is detected at the detector 40 when the length of the reference arm 17 within the coherence length of the light source 10 is equal to the length of a subsequent area of the system 1 referred to as the test arm 41. The test arm 41 comprises the fiber 14, the lens 26, the diffractive optical element 27, the beam splitter 28 and the eye 2 whose length L is to be measured.

Figure 5:
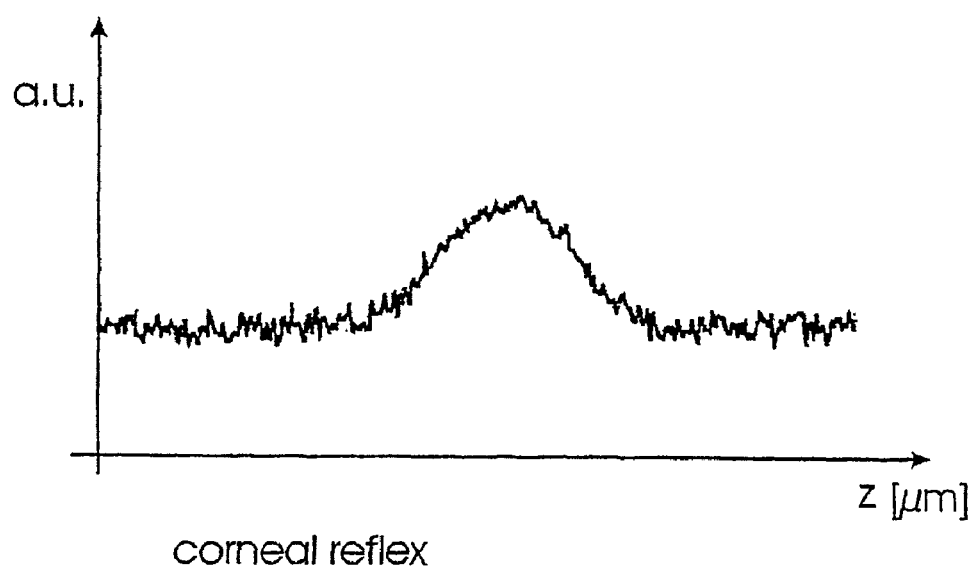
FIG. 5 shows an envelope curve of an interference signal of the cornea.
Figure 6:
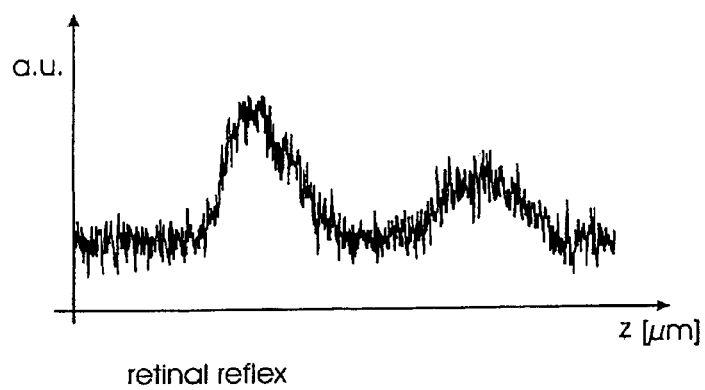
FIG. 6 shows an envelope curve of an interference signal of the retina.

When the length of the reference arm 17 equals the length of the test arm 41 with the secondary light source 29 on the retina 6 as end point, a signal (retinal reflection) which, in principle, looks like that shown in FIG. 6 is detected at the detector 40. On the other hand, when the length of the reference arm 17 equals the length of the test arm 41 with the reflection from the surface 4' of the cornea 4 as end point, a signal (corneal reflection) is detected which, in principle, corresponds to that shown in FIG. 5.

Further, the length of the reference arm 17 changes by means of the revolving wheel 19 with the PMMA cylinders 22 and the diaphragm openings 20. The length 1 of the PMMA cylinders 22 is selected with 1=L/(n−1), where L, with L=n·1, is the optical length of the normal eye 2:
1 length of the PMMA cylinder 22
L length of the eye 2
s optical path length with PMMA cylinder 22
$s_0$ optical path length without PMMA cylinder 22

$$\Delta s = s - s_0 = n\cdot 1 - 1 = 1\cdot(n-1)$$

When the optical path length difference Δs is selected in such a way that it lies on the same order of magnitude (Δs=L) as the length L of the eye 2, then:

$$L = 1\cdot(n-1) \text{ or } 1 = L/(n-1)$$

With commonly occurring lengths of the normal eye 2 of a patient of L=24 mm to L=28 mm, cylinder 22 is used in the order of magnitude of 70 mm to 85 mm in the present embodiment example with an index of refraction of the PMMA material of n=1.336.

The retinal and corneal signals at the detector 40 are recorded by an analog-to-digital (AD) converter 42. This data acquisition with detector 40 and AD converter 42 is synchronized with a start signal transmitted by the controller/regulator 24 of the stepper motor 23 when the light beam in the reference arm 17 penetrates one of the PMMA cylinders 22 on the revolving wheel 19. The light beam in the reference arm 17 penetrates the PMMA cylinders 22 and the diaphragm openings 20 in a time interval T with the same duration, since the diameter of the PMMA cylinders 22 and the diaphragm openings 20 are equal.

The reflector 16 of the reference arm 17 repeatedly carries out the periodic forward and backward movement 25 during this time interval T in which the light beam of the reference arm 17 penetrates the PMMA cylinder 22. The signal coming from the detector 40 is switched to a RAM register 44 via the AD converter 42 and a duplexer 43 when the reflector 16 is moving forward, while an address pointer of the RAM register 44 counts up. However, when the reflector 16 moves backward, the address pointer of the RAM register 44 counts down.

All values that were detected while the light beam penetrated one of the PMMA cylinders 22 are combined and averaged at the respective address of the RAM register 44. The influence of interference signals and noise on the measurement can accordingly be minimized.

As soon as the light beam of the reference arm 17 penetrates one of the diaphragm openings 20 of the revolving wheel 19, the same process for forming the detection values and average values is repeated. However, the data are combined in another RAM register 45.

As is shown in FIGS. 5 and 6, the enveloping function of the interferogram can then be calculated with the Hilbert transformation. When ƒ(t) is the signal function, the Hilbert transformation H gives the imaginary part of the analog signal f with the real part ƒ(t):

$$\tilde{f}(t) = f(t) + j\cdot H\cdot\{f(t)\}.$$

The enveloping function u(t) of the signal is:

$$u(t) = |\tilde{f}(t)| = \sqrt{f^2(t) + (H\{f(t)\})^2}.$$

A possible bandwidth Δ of the movement 25 of the reflector 16 is selected in such a way that L±Δ/2 covers the anticipated eye length distribution of the patient population, which is generally between 24 mm and 28 mm. The site of the center of the corneal reflection and the retinal reflection is calculated from data vectors which were plotted during time interval T in a central data processing unit 46 carrying out all calculation and control. The signal corresponding to the reflection of the retina 6 comprises two reflections according to FIG. 6. The first and larger of these reflections originates from the epithelial pigment, or pars pigmentosa, which is located directly behind the receiver layer of the retina 6. The second and smaller of the reflections, however, originates from the pars nervosa, a nervous layer arranged directly in front of the receiver layer of the retina 6. For measurement of the eye length L, the average of the positions of the two peaks can be used for the position of the retina, since the two layers, the pars pigmentosa and pas nervosa, are arranged very close together and their average position corresponds in practice to the position of the retina 6. The signal corresponding to the reflection of the cornea 4 comprises only one reflection of the surface 4' of the cornea 4, the anterior epithelium, so that the position of the cornea 4 can be used directly.

The eye length L is then calculated from the difference between the two positions.

While the foregoing description and drawings represent the present invention, it will be obvious to those skilled in the art that various changes may be made therein without departing from the true spirit and scope of the present invention.

The invention claimed is:

1. A system for contactless measurement of the optical imaging quality of an eye comprising:
   a light source;
   an interferometer by which at least one light pulse with a short coherence length is coupled into the eye from said light source;
   a detector;
   the optical path length of at least one arm of the interferometer being varied for measuring the length (L) of the eye until a typical interference pattern between a reflection of the cornea and a reflection of the retina of the eye occurs in said detector;
   said interference pattern together with a known path segment of the variation ($\Delta s$) of the optical path length allowing conclusions to be made about the length (L) of the eye; and
   the variation ($\Delta s$) of the optical path length is determined by introducing at least one partially optically transparent elements and at least one element of the interferometer which is movable in a defined manner in the at least one arm of the interferometer.

2. The system according to claim 1, wherein the element of the interferometer which is movable in a defined manner is constructed as a reflector.

3. The system according to claim 2, wherein the movement of the reflector and the introduction of the at least partially optically transparent elements is carried out in the light path of the same arm of the interferometer.

4. The system according to claim 1, wherein the interferometer is constructed as a fiber-optic interferometer.

5. The system according to claim 1, wherein the reflections of the retina are sent via an optical imaging device to a device for detecting the aberrations of the wavefronts in mydriasis of the eye.

6. The system according to claim 5, wherein the device for detecting the aberrations of the wavefronts in mydriasis of the eye is constructed as a Hartmann-Shack sensor.

7. The system according to claim 1, wherein the reflector is moved by a driving device so as to be measurable in its linear position.

8. The system according to claim 1, wherein the elements which are at least partially optically transparent are constructed as cylinders of polymethylmethacrylate.

9. The system according to claim 8, wherein the cylinders are arranged on an axis of a wheel which is arranged so as to be at least partially vertical to the optical axis of the reflector.

10. The system according to claim 9, wherein one of the cylinders in each instance can be selectively swiveled into the light path on a wheel in the manner of a turret drum.

11. The system according to claim 9, wherein the wheel is driven by a stepper motor.

12. The system according to claim 9, wherein diaphragm openings and cylinders are arranged alternately on the wheel.

13. The system according to claim 1, wherein a superluminescent diode serves as the light source.

14. The system according to claim 4, wherein the light from one end of a fiber of the interferometer reaches the eye via an optical imaging device.

15. The system according to claim 14, wherein the imaging device has at least one lens.

16. The system according to claim 14, wherein the imaging device has at least one diffractive optical element.

17. The system according to claim 14, wherein the imaging device has at least one beam splitter for coupling into the device for detecting the aberrations of the wavefronts.

18. The system according to claim 16, wherein the diffractive optical element is constructed in such a way that the first diffraction order is focused on the surface of the cornea.

19. The system according to claim 16, wherein the Hartmann-Shack sensor has a lens array and a detector field.

20. The system according to claim 19, wherein the detector field is constructed with CCD sensors.

21. The system according to claim 1, further comprises at least one electronic data processing device for detecting and evaluating measurement data and for controlling or regulating the movement path of the reflector.

* * * * *